United States Patent [19]

Bisnaire et al.

[11] Patent Number: 5,752,520

[45] Date of Patent: May 19, 1998

[54] LASER LEVELLING DEVICE

[75] Inventors: Deborah Bisnaire; Lynda Robinson, both of London; Mark Studenny, Ilderton; Bob Petrosenko, London, all of Canada

[73] Assignee: University Hospital, London, Canada

[21] Appl. No.: 481,973

[22] Filed: Jun. 7, 1995

[51] Int. Cl.⁶ .................................................. A61B 5/02
[52] U.S. Cl. .................. 128/672; 128/673; 606/2
[58] Field of Search .................... 128/672–675, 128/748; 606/15, 16, 2; 33/379

[56] References Cited

U.S. PATENT DOCUMENTS 5,280,789  1/1994  Potts ............................ 128/672 X Primary Examiner—Jennifer Bahr
Assistant Examiner—Ryan Carter
Attorney, Agent, or Firm—Rogers & Wells

[57] ABSTRACT

A laser levelling device for use in conjunction with apparatus for evaluation of compartment pressures of a patient, and a process. The evaluation includes at least one of diagnosis, monitoring and drainage, especially using intracranial, intravascular, intracardiac, intrapulmonary or intrafascial compartments of a patient.

18 Claims, 2 Drawing Sheets

LASER LEVELLING DEVICE

FIELD OF THE INVENTION

The present invention relates to apparatus for use in the evaluation of a patient, particularly in the positioning of medical apparatus used to monitor pressures in various sections of a patient's body. Such sections are frequently referred to herein as body compartments e.g. intracranial, intravascular, intrafascial and intrapulmonary body compartments. The invention also relates to the positioning of apparatus used to drain fluid in a controlled manner to a predetermined pressure level from body compartments e.g. from an intracranial compartment. The apparatus has a laser levelling device, which may be used for both positioning and for the monitoring of the position of the apparatus.

BACKGROUND TO THE INVENTION

In any of these uses or applications, the drainage or pressure evaluation apparatus must be aligned or positioned level with a designated anatomical landmark on the patient specific to the compartment being measured or drained. Correct and consistent levelling of this apparatus is essential in order to ensure accurate pressure assessment. Measured pressures and subsequent patient management decisions are dependent on precise alignment with the appropriate landmark.

Because of the nature of the existing levelling apparatus and concern for patient safety and comfort, many of these monitoring and drainage devices are mounted on a pole at the bedside, rather than being attached directly to the patient. Therefore, correct positioning of the apparatus relative to a landmark on the patient must be estimated visually or ascertained with some type of levelling tool over some distance viz. from a pole to the patient and often around and through many other pieces of apparatus and obstacles. The tool that is currently used most frequently for the levelling procedure is a standard carpenter's level. However, use of a carpenter's level is unsatisfactory as it presents some hazard to the patient e.g. hard, sharp edges and it is difficult to manipulate around bedrails and other apparatus. In addition, checking the level and then adjusting the apparatus position is a multi-hand and often multi-trial task that is time consuming for caregivers.

SUMMARY OF THE INVENTION

Apparatus that is capable of accurately positioning and/or of monitoring the positioning of apparatus used in evaluation of a patient has now been found.

Accordingly, the present invention provides a laser levelling device for use in conjunction with apparatus for evaluation of compartment pressures of a patient, in which the position of the apparatus relative to the patient must be monitored, maintained at and/or adjusted to a predetermined height, said device having means for attachment to said apparatus such that the beam of said laser is horizontal and at a predetermined position on said apparatus, the apparatus being adjustable vertically so that the apparatus may be located at said predetermined height.

The present invention also provides apparatus for evaluation of compartment pressures of a patient, in which the position of the apparatus relative to the patient must be monitored, maintained at and/or adjusted to a predetermined height, the improvement comprising attaching a laser levelling device to said apparatus, such that the beam of said laser is horizontal and at a predetermined position on said apparatus, the apparatus being adjustable vertically so that the apparatus may be located at said predetermined height.

The present invention further provides a process for evaluation of compartment pressures of a patient, in which the position of apparatus for said evaluation relative to the patient must be monitored, maintained at and/or adjusted to a predetermined height, the improvement comprising positioning said apparatus using a laser levelling device attached to said apparatus, such that the beam of said laser is horizontal and at a predetermined position on said apparatus, adjusting said apparatus vertically so that the apparatus is located at said predetermined height.

In preferred embodiments of the invention, the apparatus is used in medical evaluation of a patient that includes at least one of diagnosis, monitoring and drainage of a compartment of the patient.

In a further embodiment, fluid pressure is regulated or monitored.

DETAILED DESCRIPTION OF THE INVENTION

Figure 1:
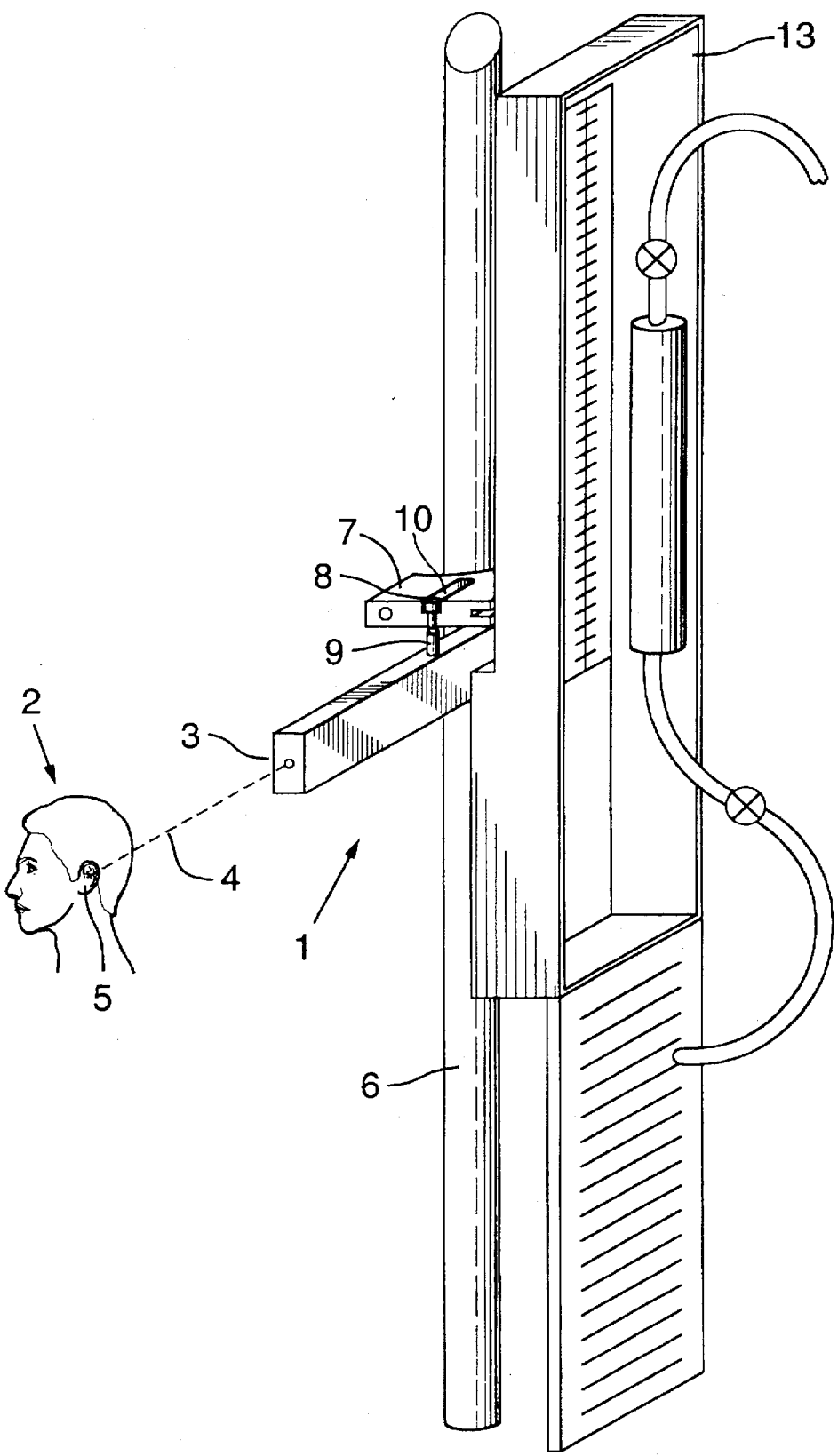

The laser levelling device of the present invention will be described herein with particular reference to one type of pressure drainage device viz. a Codman II ventricular drainage system. This pressure drainage device is an example of medical apparatus used to measure and/or drain the intracranial compartment of a patient, specifically the intraventricular compartment of the patient. It will be appreciated, however, that the laser levelling device may be used with other existing apparatus, or apparatus to be developed, in evaluation of a patient by monitoring or controlling the pressure within a compartment of the patient.

To use the Codman II ventricular drainage system for either pressure measurement or fluid drainage, it must be placed on a pole such that the zero or reference point on the apparatus is level with an appropriate anatomical landmark, in this instance the external auditory meatus of the patient. The laser levelling device is attached to the apparatus, for example via a clamp, such that the laser light beam is located and levels at the zero or reference point of the apparatus. In this manner, with the laser levelling device and the apparatus appropriately connected together, it is possible for a caregiver to simultaneously achieve correct placement of the apparatus by movement of the laser levelling device and the Codman II system by means of a common pole attachment clamp.

Figure 2:
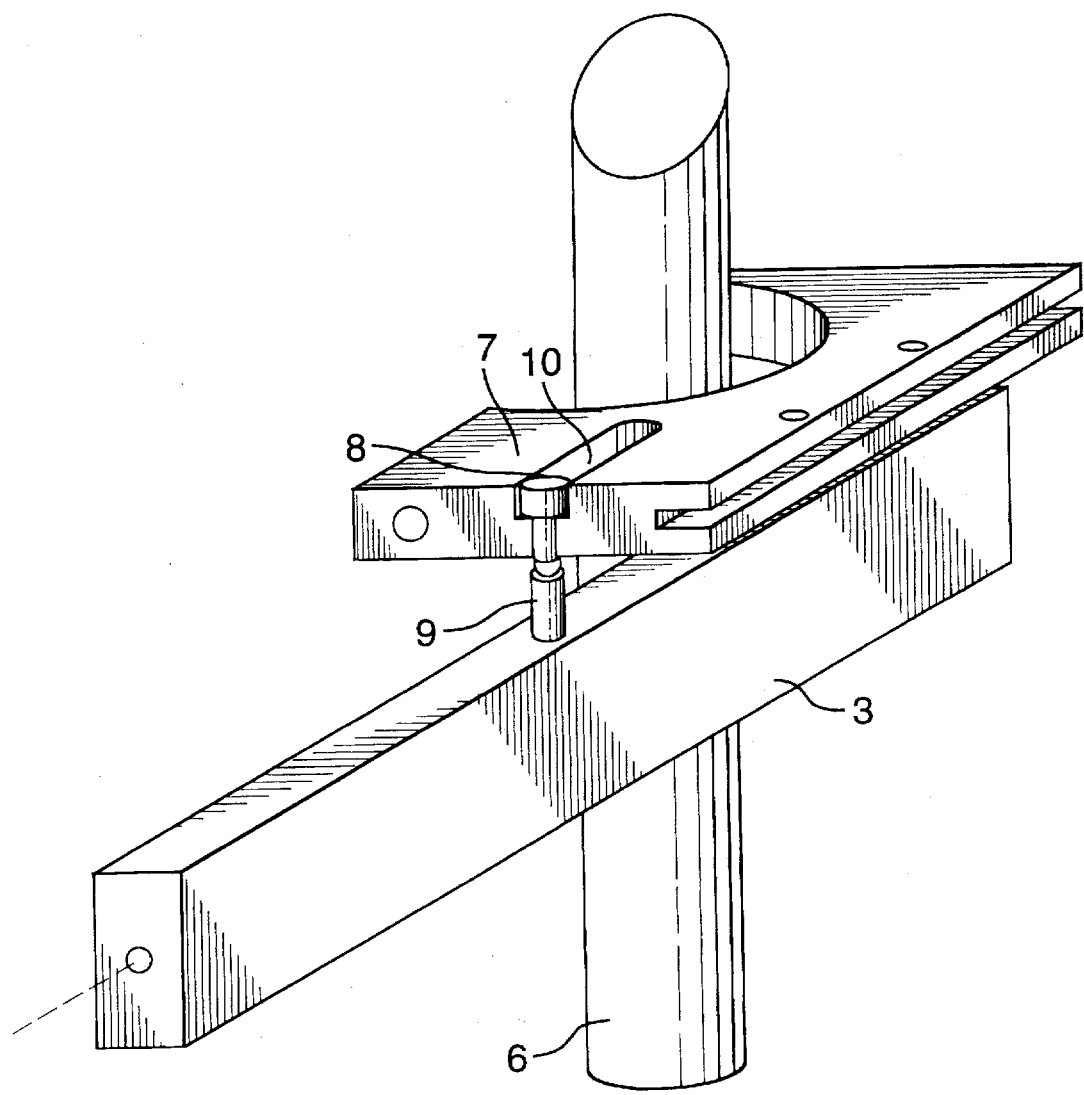

The present invention is illustrated by the embodiments shown in the drawings in which:

FIG. 1 is a schematic representation of a laser levelling device aligned with the external auditory meatus of a patient; and FIG. 2 is a schematic representation of the laser levelling device attachment to the clamp holder of the Codman II ventricular collection system.

The present invention will be described with particular reference to using the external auditory meatus as the reference point on the patient, although other reference points may be selected according to the compartment being evaluated.

FIG. 1 shows a laser levelling device system 1 aligned with a patient 2. Laser beam 4 of laser 3 is shown as being aligned with the external auditory meatus 5 of patient 2. Laser 3 is attached to pole 6 by means of universal joint 9 having attachments 8 on the upper end thereof. Attachment 8 is located in slot 10 of clamp 7, more clearly shown in FIG.

2. Attachment 8 and use of universal joint 9 is intended to provide a consistent positioning of laser 3, in a horizontal position. Slot 10 of clamp 7 is fabricated such that when laser 3 is mounted on clamp 7, laser beam 4 is aligned with the zero or reference point on pressure regulator 13. The lower end of universal joint 9 is attached to laser 3 in a balanced manner to ensure that laser 3 will position itself horizontally. However, it should be understood that the method of attachment of the laser to the clamp may be varied, provided that the means of attachment is capable of consistently locating the laser in the same location and of keeping the laser in a horizontal position. Both consistency of positioning of the laser on the apparatus and consistency of positioning of the laser in a level position are important. An indicator that shows whether the laser is level e.g. a bubble in a liquid in a suitable enclosure, may be added to the exterior of the laser for checking that the laser is level. Many lasers suitable for use in this invention have a bubble level indicator thereon when purchased. It is preferred that the laser automatically be held in the horizontal position, so that it is not necessary for a person to need to adjust the laser to the horizontal.

In the embodiment shown in FIG. 1, clamp 7 also holds the Codman II ventricular drainage collection system.

FIG. 2 shows an embodiment of a method of attachment of laser 3 to clamp 7. Laser 3 has universal joint 9 connected thereto to attachment 8. Attachment 8 is located in slot 10 of clamp 7. Universal joint 9 is free to move so that laser 3 will reset in a horizontal position. As noted above, other methods of attachment of laser 3 to clamp 7 may be used, including self-levelling ball-bearing systems or the like such that laser 3 stabilises in a horizontal position.

In operation of the particular embodiment of the drawings, laser 3 is attached by inserting attachment 8 into slot 10 of clamp 7, such that universal joint 9 becomes positioned in slot 10. The same laser could be used for levelling a variety of pieces of apparatus, i.e. the same laser could be moved from apparatus to apparatus for checking that each apparatus is correctly located with respect to the respective patient's appropriate anatomical landmark. Thus, it is convenient that the attachment of the laser to the clamp provide both a simple and automatic levelling of the laser device as well as easy attachment and detachment to the clamp. It is to be understood that clamp 7 could be moved up or down pole 6 in order to locate laser 3 in the correct position opposite, for example, the external auditory meatus of the patient.

While the laser levelling device has been described with respect to use with an available intracranial compartment measurement and drainage system, the device may be used with other apparatus requiring accurate and consistent positioning with respect to the patient. Other pressure compartments include but are not limited to a patient's intravascular, intracranial, intrapulmonary, intrafascial compartments. The uses include both drainage and monitoring e.g. measurement of pressure within a patient's compartment.

The laser should be of a type that does not require the use of eye protection during use. While lasers requiring eye protection could be used, it is preferred for ease of use and safety of the user and the patient that the laser not require the use of eye protection. For example, the laser may be a Class IIIa diode laser, which is commercially available; as used herein, the classification of the laser, especially as a Class IIIa laser, is according to the definitions of the American National Standards Institute (ANSI) of New York, N.Y.

The clamp of the laser levelling device should be fabricated such that the zero or reference point on the existing apparatus is located at the same level as the laser light beam. It may be preferable as shown in the embodiment particularly illustrated herein, that the laser levelling device and the existing monitoring/drainage apparatus be attached by means of the same clamp or other attachment apparatus such that a single adjustment is all that is needed to move and correctly locate both the laser levelling device and the apparatus.

The laser levelling device provides a safe and flexible means to check the positioning of the apparatus, that does not require touching of the patient or of the laser per se by a caregiver, and moreover which may be used in situations where only a narrow visual path exists between the apparatus and the patient. These are both significant advantages over existing techniques. In addition, because it can attach directly to the apparatus and because it is self-levelling, the process of checking and adjusting position of the apparatus can be completed by a single caregiver in a single step. Thus, it is a more effective and time efficient method of positioning and monitoring the position of apparatus with respect to a patient.

We claim:

1. A laser leveling device for use in conjunction with apparatus for evaluation of compartment pressures of a patient, in which the position of the apparatus relative to the patient must be monitored, maintained at and/or adjusted to a predetermined height, said laser levelling device having a laser capable of emitting a laser beam, said device having self-levelling means for attachment to said apparatus such that the beam of said laser is consistently positioned horizontally and at a predetermined position on said apparatus.

2. The laser levelling device of claim 1 in which the self-adjusting means includes a universal joint.

3. The laser levelling device of claim 2 in which the universal joint is supported in a slot in said apparatus, said laser being suspended from said universal joint.

4. The device of claim 2 in which the laser is a Class IIIa diode laser.

5. The device of claim 4 in which the apparatus is for medical evaluation that includes at least one of diagnosis, monitoring and drainage.

6. The device of claim 5 in which the apparatus is utilized in evaluation of intracranial, intravascular, intracardiac, intrapulmonary or intrafascial compartments of a patient.

7. In an apparatus for evaluation of compartment pressures of a patient, in which the apparatus must be positioned or aligned level with an anatomical landmark on the patient specific to the compartment and in which the apparatus has a zero or reference point level with the anatomical landmark, and in which the position of the apparatus relative to the patient must be monitored, maintained at and/or adjusted to a predetermined height, the improvement comprising a laser levelling device attached to said apparatus, said laser levelling device having a laser capable of emitting a laser beam and said laser being suspended therefrom such that the beam of said laser is horizontal and at a predetermined position on said apparatus, the apparatus being adjustable vertically so that the apparatus may be located at said predetermined height.

8. The apparatus of claim 7 in which the laser is suspended from a universal joint located in a slot in said apparatus.

9. The apparatus of claim 8 in which the medical evaluation includes at least one of diagnosis, monitoring and drainage.

10. The apparatus of claim 9 where positioned with reference to an anatomical landmark of the patient appropriate to evaluation of said compartment pressure.

11. The apparatus of claim 9 in which the laser is a Class IIIa diode laser.

12. The apparatus of claim 11 where utilized in evaluation of intracranial, intravascular, intracardiac, intrapulmonary or intrafascial compartments of a patient.

13. In a process for evaluation of compartment pressures of a patient, in which an apparatus must be positioned or aligned level with an anatomical landmark on the patient specific to the compartment and in which the apparatus has a zero or reference point level with the anatomical landmark, and in which the position of apparatus for said evaluation relative to the patient must be monitored, maintained at and/or adjusted to a predetermined height, the improvement comprising positioning said apparatus using a laser levelling device attached to said apparatus for positioning said apparatus; said laser levelling device having a laser capable of emitting a laser beam and said laser being suspended therefrom such that the beam of said laser is horizontal and at a predetermined position on said apparatus, adjusting said apparatus vertically so that the apparatus is located at said predetermined height.

14. The process of claim 13 in which the medical evaluation includes at least one of diagnosis, monitoring and drainage.

15. The process of claim 14 in which the laser is a Class IIIa diode laser.

16. The process of claim 15 where utilized in evaluation of intracranial, intravascular, intracardiac, intrapulmonary or intrafascial compartments of a patient.

17. The process of claim 14 where the apparatus is positioned with reference to an anatomical landmark of the patient appropriate to evaluation of said compartment pressure.

18. The process of claim 17 in which fluid pressure is regulated or monitored.

\* \* \* \* \*